United States Patent
Takeda et al.

(10) Patent No.: US 6,172,266 B1
(45) Date of Patent: Jan. 9, 2001

(54) TRIAZOLE DERIVATIVE OR SLAT THEREOF, PREPARATION PROCESS THEREOF AND PHARMACEUTICAL CONTAINING SAID COMPOUND AS AN EFFECTIVE INGREDIENT

(75) Inventors: Sunao Takeda, Ichihara; Yasushi Kaneko, Narita; Minoru Tokizawa, Narita; Hiromichi Eto, Narita; Kazuya Ishida, Narita; Kazunori Maebashi, Narashino; Masaru Matsumoto, Inba-gun; Takemitsu Asaoka, Narita; Susumu Sato, Narita, all of (JP)

(73) Assignee: SSP Co., Ltd., Tokyo (JP)

( * ) Notice: Under 35 U.S.C. 154(b), the term of this patent shall be extended for 0 days.

(21) Appl. No.: 09/471,286

(22) Filed: Dec. 23, 1999

Related U.S. Application Data

(62) Division of application No. 09/235,320, filed on Jan. 22, 1999, now Pat. No. 6,040,325.

(30) Foreign Application Priority Data

Feb. 2, 1998 (JP) .................................................. 10-020690

(51) Int. Cl.$^7$ ................................................. C07C 323/07
(52) U.S. Cl. .................................................................. 568/43
(58) Field of Search .................................................. 568/43

(56) References Cited

U.S. PATENT DOCUMENTS

| 5,939,448 | 8/1999 | Tokizawa et al. . |
| 5,945,438 | 8/1999 | Tokizawa et al. . |
| 5,986,144 | 11/1999 | Tokizawa et al. . |
| 6,002,028 | 12/1999 | Tokizwa et al. . |
| 6,008,239 | 12/1999 | Kaneko et al. . |
| 6,040,325 | 3/2000 | Takeda et al. . |

FOREIGN PATENT DOCUMENTS

| 0 140 154 | 5/1985 | (EP) . |
| 0 435 081 | 7/1991 | (EP) . |
| 0 473 387 | 8/1991 | (EP) . |
| 0 780 380 | 6/1997 | (EP) . |
| 0 814 079 | 12/1997 | (EP) . |

OTHER PUBLICATIONS

Miyauchi, H, et al., "Synthesis and antifungal activities of opticlly activities of optically active isomers of SM–8668," *Bioorganic & Medicinal Chemistry Letters,* vol. 5, No. 9, pp. 933–936, May 4, 1995.

Miyauchi, H, et al., "Structure–activity relationships of sulfur–containing triazole antifungals," *Bioorganic & Medicinal Chemistry Letters,* vol. 5, No 14., pp. 1479–1482, July 20, 1995.

*Primary Examiner*—Patricia L. Morris
(74) *Attorney, Agent, or Firm*—Oblon, Spivak, McClelland, Maier & Neustadt, P.C.

(57) ABSTRACT

Described is a triazole derivative represented by the formula (1):

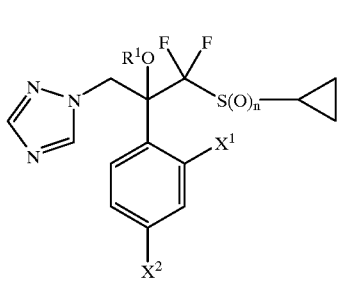

wherein $R^1$ represents a hydrogen atom, a lower alkyl group or an aralkyl group, $X^1$ and $X^2$ are the same or different and each independently represents a hydrogen atom, a halogen atom or a halogenoalkyl and n stands for an integer of 0 to 2, or salt thereof; a preparation process of said compound and a pharmaceutical comprising said compound as an effective ingredient.

The compound as described above has high antimycotic activity and is useful for the prevention and treatment of mammalian mycotic infections.

1 Claim, No Drawings

TRIAZOLE DERIVATIVE OR SLAT THEREOF, PREPARATION PROCESS THEREOF AND PHARMACEUTICAL CONTAINING SAID COMPOUND AS AN EFFECTIVE INGREDIENT

This application division of application Ser. No. 09/235,320 filed on Jan. 22, 1999, now Pat. No. 6,040,325.

BACKGROUND OF THE INVENTION

1. Field of the Invention

This invention relates to a triazole derivative or salt thereof which has excellent antimycotic action and high safety, an intermediate for preparing said compound and a pharmaceutical comprising said compound as an effective ingredient.

2. Description of the Related Art

Mycosis can be classified into two types, that is, superficial mycosis represented by various trichophytosis, marginated eczema, psoriasis, cutaneous candidiasis or the like and deep seated mycosis represented by mycotic meningitis, mycotic infectious disease of respiratory organ, fungemia, mycosis of urinary tract or the like. Of these, deep seated mycosis such as candidiasis or aspergillosis tends to show a marked increase in recent days owing to the frequent use of an anticancer chemotherapeutic agent or immunosuppressive agent or lowering in the bioimmunology due to HIV infection or the like. There is accordingly a demand for a pharmaceutical efficacious against fungi causing such diseases.

As pharmaceuticals effective against Aspergillus spp. and Candida spp., Amphotericin B and azole base compounds such as Fluconazole and Itraconazole are conventionally known, but not so many pharmaceuticals have been commercially available yet. In addition, the above-exemplified pharmaceuticals involve problems in safety and antimycotic action. There is accordingly a demand for an antimycotic effective against Aspergillus spp. and Candida spp. Now, more effective azole base compounds are under development. For example, as a compound having a difluoromethylene group, those described in Japanese Patent Application Laid-Open Nos. 163374/1984, 163269/1993 and 227531/1997 are known. As an azole base compound having a substituted ter-tiary hydroxyl group, cyclic compounds as described in Japanese Patent Application Laid-Open Nos. 217778/1996 and 333367/1996, acyl compounds as described in Japanese Patent Application Laid-Open Nos. 104676/1996 and 183769/1997, and the like are known but they are not fully satisfactory.

SUMMARY OF THE INVENTION

Accordingly, an object of the present invention is to provide a compound which has high safety and has antimycotic activity effective against Aspergillus spp. and Candida spp.

With the forgoing in view, the present inventors synthesized a number of triazole derivatives and salts thereof and carried out an investigation on their antimycotic activity effective against Aspergillus spp. and Candida spp. As a result, it has been found that a cyclopropylthio- or cyclopropylsulfonyl-containing triazole derivative represented by the below-described formula (1) and a salt thereof are superior in antimycotic activity against fungi including Aspergillus spp. and Candida spp. and also in safety to the analogous compounds which have been known to date, leading to the completion of the present invention. In one aspect of the present invention, there are thus provided a triazole derivative represented by the following formula (1):

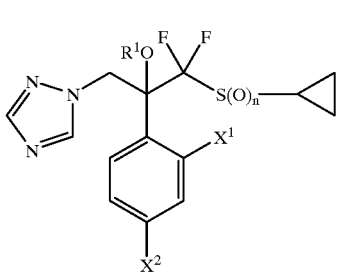

(1)

wherein $R^1$ represents a hydrogen atom, lower alkyl group or aralkyl group, $X^1$ and $X^2$ are the same or different and each independently represents a hydrogen atom, a halogen atom or a halogenoalkyl group and n stands for an integer of 0 to 2, or salt thereof; an intermediate for preparing said compound; and a preparation process of these compounds.

In another aspect of the present invention, there is also provided a pharmaceutical comprising as an effective ingredient the triazole derivative represented by the formula (1) or salt thereof.

In a further aspect of the present invention, there is also provided a pharmaceutical composition comprising the triazole derivative represented by the formula (1) or salt thereof and a pharmacologically acceptable carrier.

In a still further aspect of the present invention, there is also provided the use of the triazole derivative represented by the formula (1) or salt thereof as a pharmaceutical.

In a still further aspect of the present invention, there is also provided a treating method of mycotic infections, which comprises administering to a patient a pharmacologically effective amount of the triazole derivative represented by the formula (1) or salt thereof.

The triazole derivative or salt thereof according to the present invention has strong antimycotic activity, and an antimycotic comprising such compound as an effective ingredient is useful for the prevention and treatment of mycotic infections of mammary animals including humans.

BRIEF DESCRIPTION OF THE PREFERRED EMBODIMENTS

In the triazole derivative of the present invention, examples of the lower alkyl group represented by $R^1$ in the formula (1) include linear or branched $C_{1-6}$ alkyl groups. Specific examples include methyl, ethyl, n-propyl, i-propyl, n-butyl, i-butyl, sec-butyl, t-butyl, n-pentyl, i-pentyl and n-hexyl. As the aralkyl group represented by $R^1$, $C_{7-10}$ aralkyl groups are preferred, with phenyl-$C_{1-4}$ alkyl groups being more preferred. Specific examples include benzyl, phenethyl and phenylpropyl. As $R^1$, methyl and benzyl groups are preferred. In $X^1$ or $X^2$, examples of the halogen atom include fluorine, chlorine, bromine and iodine atoms, with the fluorine and chlorine atoms being particularly preferred. Examples of the halogenoalkyl group include the above-exemplified $C_{1-6}$ alkyl groups each substituted by the above-exemplified halogen atom. Among them, perfluoro-$C_{1-6}$ alkyl groups are preferred, with trifluoromethyl and pentafluoroethyl groups being particularly preferred and trifluoromethyl group being more preferred. The number n of oxygen atoms stands for an integer of 0 to 2, with 0 or 2 being preferred.

No particular limitation is imposed on the salt of the triazole derivative (1) of the present invention insofar as it is a pharmacologically acceptable salt. Examples include acid addition salts such as hydrochlorides, nitrates, hydrobromides, p-toluenesulfonates, methanesulfonates, fumarates, succinates and lactates.

The triazole derivative (1) or salt thereof according to the present invention has stereoisomers based on its asymmetric carbon and sulfoxide. The present invention embraces any one of such isomers and isomer mixtures such as racemic modifications. The triazole derivative (1) or salt thereof may exist in the form of a solvate typified by a hydrate. The present invention also embraces solvates of these compounds.

The triazole derivative (1) of the present invention can be prepared, for example, in accordance with the reaction scheme described below:

In the above preparation process, the 2,2-difluoro-2-cyclopropylthioacetophenone derivative represented by the formula (2) and oxirane derivative represented by the formula (3) are novel compounds synthesized by the present inventors and are useful as an intermediate for the synthesis of a triazole derivative (1).

The present invention will hereinafter be described in accordance with the above steps.

Step (5-4):

Compound (4) can be prepared by introducing a cyclopropylthio group into Compound (5).

In Compound (5) employed as a starting material, examples of $X^3$ in the formula (5) include fluorine, chlorine and bromine atoms. Among them, chlorine and bromine atoms are preferred. Compound (5) which contains as $X^3$ a fluorine, chlorine or bromine atom and as $X^1$ and $X^2$ a

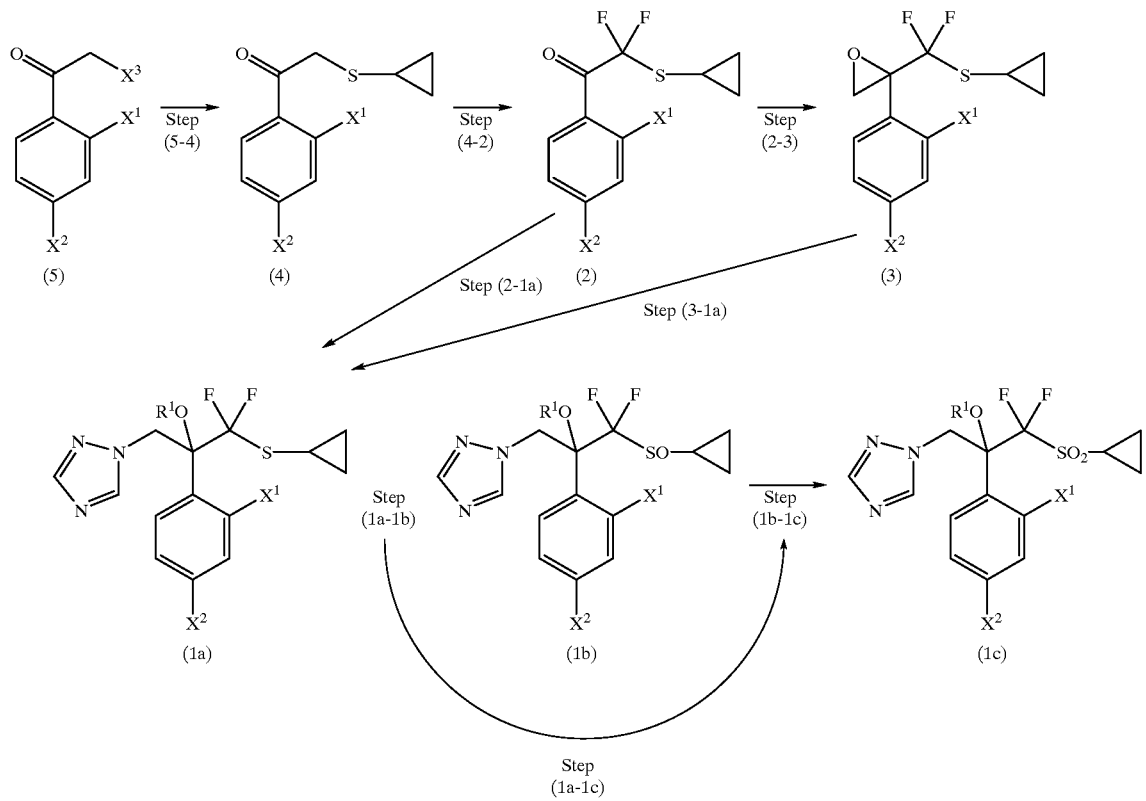

wherein $R^1$, $X^1$ and $X^2$ have the same meanings as defined above and $X^3$ represents a halogen atom.

Described specifically, Compound (1a), that is, a compound of the formula (1) wherein n stands for 0 can be prepared by introducing a cyclopropylthio group into a 2-haloacetophenone derivative (5) which is a known compound; difluorinating the resulting cyclopropylthio compound (4) into Compound (2); and directly introducing a triazolemethyl group into Compound (2) or first introducing an epoxymethylene group into Compound (2) to obtain Compound (3) and then introducing a triazole group into Compound (3). The $R^1$ of the resulting Compound (1a) can be alkylated or aralkylated as desired. By the oxidation of Compound (1a), Compound (1b), that is, a compound of the formula (1) wherein n stands for 1 or Compound (1c), that is, a compound of the formula (1) wherein n stands for 2 can be prepared. Alternatively, Compound (1c) can be prepared by the oxidation of Compound (1b).

fluorine atom are commercially available, for example, from Aldrich Chemical Co., Inc.

Compound (4) can be prepared by reacting Compound (5) with a cyclopropylthio-introducing agent in the presence of a base. As the cyclopropylthio-introducing agent, cyclopropylmercaptane [J. Am. Chem. Soc., 114, 3492(1992)] is preferred. Examples of the reaction solvent include methanol, ethanol, diethyl ether, a methanol-diethyl ether solvent mixture, N,N-dimethylformamide, 1,4-dioxane and tetrahydrofuran, with methanol and methanol-diethyl ether solvent mixture being particularly preferred. As the base, any one of sodium carbonate, potassium carbonate, sodium hydroxide, potassium hydroxide, barium hydroxide, sodium hydride, potassium hydride, sodium methoxide, sodium ethoxide, pyridine, triethylamine and the like is usable, with potassium carbonate being preferred.

Step (4-2)

Compound (2) can be prepared by reacting Compound (4) with a fluorinating reagent in a solvent.

Examples of the fluorinating agent include fluorine gas, perchloryl fluoride, potassium fluoride, spray-dried potassium fluoride, freeze-dried potassium fluoride, tetraalkylammonium fluoride, tris(dimethylamino)-sulfa(trimethylsilyl) difluoride, N-fluoropyridone, N-fluoro-N-alkyl-arenesulfonamide, N-fluoroquinuclidinium salt, N-fluoroperfluoroalkyl sulfonimide, N-fluorosaltum, fluorinated xenon, N-fluoropyridinium salt and N-fluoropyridinium sulfonate. Examples of the commercially available fluorinating reagent include "Onoda Fluorinates FP-T300, FP-T500, FP-T700, FP-B300, FP-B500, FP-B700 and FP-B800" (trade names; products of Chichibu Onoda Co., Ltd.) and "MEC-01, MEC-02, MEC-03, MEC-04 and MEC-05" (trade names; products of Daikin Industries, Ltd.). It is preferred to use the fluorinating reagent in an amount of 2 to 20 equivalents per mole of Compound (4). Illustrative of the reaction solvent include 1,2-dichloroethane, 1,1,2-trichloroethane, chloroform, methylene chloride, diethyl ether, ethyl acetate and tetrahydrofuran. Among them, 1,1,2-trichloroethane is preferred. The reaction temperature is −78° C. to the boiling point of the solvent, with 80 to 100° C. being preferred.

To improve the yield of the compound, a Lewis acid or a base can be used. Exemplary Lewis acids include aluminum chloride, zinc chloride and stannic chloride, while exemplary bases include sodium hydroxide, potassium hydroxide, barium hydroxide, sodium carbonate, potassium carbonate, sodium hydride, potassium tert-butoxide, lithium diisopropylamide and potassium hexamethyldisilazane.

Step (2-1a):

Direct synthesis from Compound (2) to Compound (1a) is carried out by reacting 1 mole of Compound (2) with 1 to 5 moles of an epoxymethylating agent and 1 to 4 moles of 1,2,4-triazole or alkaline metal salt thereof at −100° C. to room temperature or boiling point of the solvent for 1 to 30 hours in a solvent. Examples of the epoxymethylating agent include trimethylsulfoxonium iodide and trimethylsulfonium iodide. Examples of the base include sodium hydroxide, potassium hydroxide, barium hydroxide, sodium methoxide, sodium carbonate, potassium carbonate and sodium hydride, with potassium hydroxide being particularly preferred. As the solvent, methanol, ethanol, isopropanol, n-butanol, sec-butanol, t-butanol and the like are preferred.

Step (2-3)

Compound (1a) can be prepared via Compound (3).

Compound (3) can be obtained by reacting, in a solvent, Compound (2) with 1 to 2 equivalents of an epoxymethylating agent such as trimethylsulfoxonium iodide or trimethylsulfonium iodide in the presence of 1 to 5 equivalents of an alkali. Dimethylsulfoxide, tetrahydrofuran or the like can be suitably used as a solvent. Examples of the base include sodium hydroxide, potassium hydroxide, barium hydroxide, sodium methoxide, sodium ethoxide, sodium carbonate, potassium carbonate and sodium hydride, with sodium hydride being particularly preferred. The reaction temperature preferably ranges from −100° C. to the boiling point of the solvent, with a range of from −40 to 50° C. being particularly preferred.

Step (3-1a):

Compound (1a) can be prepared by reacting Compound (3) with 1,2,4-triazole or alkali metal salt thereof in a solvent in the presence of a base. Preferred examples of the solvent include N,N-dimethylformamide, acetonitrile, N,N-dimethlacetamide and dimethylsulfoxide. Examples of the base include sodium hydroxide, potassium hydroxide, barium hydroxide, sodium carbonate, potassium carbonate and tert-butoxy potassium. The reaction temperature preferably ranges from 0° C. to the boiling point of the solvent, with a range of 20 to 60° C. being particularly preferred.

The tertiary hydroxyl group of Compound (1a) can be alkylated as needed in the presence of a base. Examples of the alkyl halide to be used for the alkylation include methyl iodide, ethyl iodide, propyl iodide and benzyl chloride. Examples of the base include sodium hydroxide, potassium hydroxide, barium hydroxide, sodium carbonate, potassium carbonate and sodium hydride. Examples of the solvent include alcoholic solvents such as methanol and ethanol, nonaqueous polar solvents such as N,N-dimethylformamide and ether solvents such as 1,4-dioxane and tetrahydrofuran, with N,N-dimethylformamide being particularly preferred. The reaction temperature preferably ranges from −40° C. to the boiling point of the solvent, with 0 to 20° C. being particularly preferred.

Step (1a–1c):

Compound (1c) can be prepared by adding at least 2 equivalents, preferably 2.2 to 2.3 equivalents of an oxidizing agent to Compound (1a). Examples of the oxidizing agent include m-chloroperbenzoic acid, aqueous hydrogen peroxide, peracetic acid, tetrapropylammonium perruthenate, osmium tetraoxide, potassium permanganate and oxone. Illustrative of the solvent include chloroform, dichloromethane, acetic acid, methanol, water, acetonitrile and carbon tetrachloride, and mixtures thereof. The reaction temperature preferably ranges from −40° C. to the boiling point of the solvent, with 0 to 50° C. being particularly preferred. To improve the yield, ruthenium trichloride, selenium dioxide, sodium tungstate, sodium molybdate and vanadium oxide may be used as a catalyst.

Step (1a–1b) and Step (1b–1c):

Compound (1b) can be prepared by adding 1 to 2 equivalents, preferably 1.2 equivalents of an oxidizing agent to Compound (1a). Examples of the oxidizing agent include m-chloroperbenzoic acid, aqueous hydrogen peroxide, peracetic acid, tetrapropylammonium perruthenate, osmium tetraoxide, potassium permanganate and oxone. Illustrative of the solvent include chloroform, dichloromethane, acetic acid, methanol, water, acetonitrile and carbon tetrachloride, and mixtures thereof. The reaction temperature preferably ranges from −40° C. to the boiling point of the solvent, with 0 to 50° C. being particularly preferred. To improve the yield, ruthenium trichloride, selenium dioxide, sodium tungstate, sodium molybdate and vanadium oxide may be used as a catalyst. Step (1b–1c) can be carried out similarly.

Compounds (1a), (1b) and (1c) each has enantiomers based on its asymmetric carbon atom. Such an optically active substance can be prepared by separating using a column for separation of an optical isomer. Examples of the optically active stationary phase include synthetic optically active polymers, natural high molecules and amino acid metal complexes. Among them, a cellulose-derivative-coated silica gel is preferred. As a column filled with this cellulose-derivative-coated silica gel, commercially-available products such as CHIRALCEL OD and CHIRALPAK AS (each, trade name; product of Daicel Chemical Industries, Ltd.) can be used, with CHIRALCEL OD being particularly preferred. As chromatography, liquid chromatography is preferred. In this case, hexane—ethanol, hexane—isopropyl alcohol, or the like can be used as an eluent as a mobile phase. The optically active substance can also be prepared by optical resolution. Examples of the reagent for optical resolution include optically active camphor-sulfonic acid or salt thereof which may be substituted with a halogen atom. Specific examples include (+)- camphor-10-sulfonic acid, (−)-camphor-10-sulfonic acid, (+)-3-bromocamphor-8-sulfonic acid, (−)-3-bromocamphor-8-sulfonic acid, (+)-3-bromocamphor-10-sulfonic acid, (−)-3-bromocamphor-10-sulfonic acid, ammonium (+)-3-bromocamphor-8-sulfonate and ammonium (−)-3-bromocamphor-8-sulfonate. Among them, (+)-3-bromocamphor-8-sulfonic acid, (−)-3-bromocamphor-8-sulfonic acid, ammonium (+)-3-bromocamphor-8-sulfonate and ammonium (−)-3-bromocamphor-8-sulfonate are particularly preferred.

No particular limitation is imposed on the isolation means of a target product from the reaction mixture available by each of the above-described reactions. The target product can be isolated, for example, by recrystallization, various types of chromatography or the like. Moreover, the target compound can be converted into a desired salt in a conventional manner.

The compound (1) of the present invention or salt thereof exhibits excellent antimycotic action against fungi including Aspergillus spp. and Candida spp. in vitro and in vivo and has high safety so that it is useful as a pharmaceutical for the prevention and treatment of mycotic infections.

From the invention compound (1), a pharmaceutical, particularly, an antimycotic can be obtained in various dosage forms such as tablets, granules, powders, capsules, suspensions, injections, suppositories and external preparations in a conventional manner. Such a pharmaceutical composition can be prepared by incorporating a pharmacologically acceptable carrier in Compound (1). Described specifically, a solid preparation can be prepared in a conventional manner by adding to the invention compound (1) an excipient and, if necessary, a binder, disintegrator, extender, coating agent, sugar-coating agent and/or the like. An injection may be prepared by dissolving, dispersing or emulsifying the invention compound (1) in an aqueous carrier such as distilled water for injection to form an injection liquid in advance or to prepare powder for injection and dissolve it upon use. Examples of the administration method of the injection include intravenous administration, intraarterial administration, subcutaneous administration and instillation.

The dose of the invention compound (1) or salt thereof as a pharmaceutical differs depending on various factors such as the kind of the disease; symptoms, weight, age or sex of the patient to be administered; or administration route. When used as an antimycotic, the pharmaceutical is used in an amount of 0.1 to 1000 mg/day, preferably 1 to 300 mg/day per adult in terms of the invention compound (1) or salt thereof. It is possible to add the above-described amount once a day or 2 to 4 portions a day.

EXAMPLES

The present invention will hereinafter be described in detail by referential examples and examples. It should however be borne in mind that the present invention will not be limited to or by the following examples.

Referential Example 1

Synthesis of 2',4'-difluoro-2-(cyclopropylthio) acetophenone [Compound (4-1)]

To a solution of 2-chloro-2',4'-difluoroacetophenone (2.8 g, 0.015 mol) in methanol (100 ml), a solution of cyclopropylmercaptane in ether, said cyclopropylmercaptane having been obtained from cyclopropyl bromide (4.8 g, 0.039 mol) by the method as described in J. Am. Chem. Soc., 114, 3492(1992), was added, followed by the addition of potassium carbonate (2.5 g, 0.018 moi) under ice cooling. The resulting mixture was stirred at room temperature for 1.5 hours. After the completion of the reaction, the solvent was distilled off under reduced pressure. Water was added to the residue, followed by extraction with ether. The extract was washed successively with water and saturated saline and dried over magnesium sulfate. The solvent was then distilled off under reduced pressure. The resulting oil was distilled under reduced pressure (120° C., 2 mmHg), whereby 2',4'-difluoro-2-(cyclopropylthio)acetophenone (2.3 g, yield: 67%) was obtained as a colorless oil.

$^1$H-NMR(CDCl$_3$, δ)

0.41–0.96(4H,m), 1.72–1.98(1H,m), 3.85(2H,d,J=2 Hz), 6.76–7.10(2H,m), 7.87–8.14(1H,m).

Referential Example 2

Synthesis of 2-(cyclopropylthio)-4'-fluoroacetophenone [Compound (4-2)]

In a similar manner to Referential Example 1 except for the use of 2-chloro-4'-fluoroacetophenone instead of 2-chloro-2',4'-difluoroacetophenone, 2-(cyclopropylthio)-4'-fluoroacetophenone was obtained as a colorless oil.

$^1$H-NMR(CDCl$_3$, δ):

0.48–1.05(4H,m), 1.86–2.03(1H,m), 3.86(2H,s), 7.04–7.26(2H,m), 7.94–8.10(2H,m).

Referential Example 3

Synthesis of 2-(cyclopropylthio)-4'-(trifluoromethyl) acetophenone [Compound (4-3)]

In a similar manner to Referential Example 1 except for the use of 2-bromo-4'-(trifluoromethyl)acetophenone instead of 2-chloro-2',4'-difluoroacetophenone, 2-(cyclopropylthio)-4'-(trifluoromethyl)acetophenone was obtained as a colorless oil.

$^1$H-NMR(CDCl$_3$, δ):

0.45–0.99(4H,m), 1.77–2.03(1H,m), 3.89(2H,s), 7.73(2H,d,J=8 Hz), 8.09(2H,d,J=8 Hz).

EXAMPLE 1

Synthesis of 2-cyclopropylthio-2,2,2',4'-tetrafluoroacetophenone [Compound (2-1)

To a solution of 2',4'-difluoro-2-(cyclopropylthio) acetophenone (13.6 g, 0.059 mol) in 1,1,2-trichloroethane (300 ml), N-fluoro-4-methylpyridinium-2-sulfonate ("MEC-02", trade name; Daikin Industries Ltd.) (29.6 g, 0.155 mol) was added in portions at an internal temperature of 90° C., followed by stirring at an internal temperature of 90 to 93° C. for 2 hours. After the completion of the reaction, the internal temperature was cooled to 500° C. or lower. Water was added to the reaction mixture, followed by extraction with 1,1,2-trichloroethane. The extract was washed successively with water and saturated saline and dried over magnesium sulfate. The solvent was then distilled off under reduced pressure. The resulting oil was subjected to chromatography on a silica gel column and from the chloroform eluate fraction, 2-cyclopropylthio-2,2,2',4'-tetrafluoroacetophenone (5.6 g, yield: 36%) was obtained as a colorless oil.

$^1$H-NMR(CDCl$_3$, δ):

0.70–1.05(4H,m), 1.94–2.29(1H,m), 6.81–7.07(2H,m), 7.85–8.11(1H,m).

EXAMPLE 2

Synthesis of 2-cyclopropylthio-2,2,4'-trifluoroacetophenone [Compound (2-2)]

In a similar manner to Example 1 except for the use of 2-(cyclopropylthio)-4'-fluoroacetophenone instead of 2',4'-difluoro-2-(cyclopropylthio)acetophenone, 2-cyclopropylthio-2,2,4'-trifluoroacetophenone was obtained as a colorless oil.

$^1$H-NMR(CDCl$_3$, δ):
0.60–1.05(4H,m), 1.98–2.24(1H,m), 7.07–7.26(2H,m), 8.10–8.26(2H,m)

EXAMPLE 3

Synthesis of 2-cyclopropylthio-2,2-difluoro-4'-(trifluoromethyl)acetophenone [Compound (2-3)]

In a similar manner to Example 1 except for the use of 2-(cyclopropylthio)-4'-(trifluoromethyl)acetophenone instead of 2',4'-difluoro-2-(cyclopropylthio)acetophenone, 2-cyclopropylthio-2,2-difluoro-4'-(trifluoromethyl)acetophenone was obtained as a colorless oil.

$^1$H-NMR(CDCl$_3$, δ):
0.61–1.13(4H,m), 1.92–2.12(1H,m), 7.76(2H,d,J=8 Hz), 8.24 (2H,d, J=8 Hz)

EXAMPLE 4

Synthesis of 2-[(cyclopropylthio)(difluoro)methyl]-2-(2,4-difluorophenyl)oxirane [Compound (3-1)]

A suspension of 60% sodium hydride (1.0 g, 0.025 mol) in tetrahydrofuran (50 ml)—dimethylsulfoxide (70 ml) was heated to an external temperature of 50° C., followed by the addition of trimethylsulfoxonium iodide (5.6 g, 0.025 mol) in portions. After stirring at the same temperature for one hour, the reaction mixture was cooled to −20° C. and added dropwise with a solution of 2-cyclopropylthio-2,2,2',4'-tetrafluoroacetophenone (5.6 g, 0.021 mol) in tetrahydrofuran (20 ml). The resulting mixture was stirred at room temperature for 2 hours. The reaction mixture was then poured into ice water, followed by extraction with ethyl acetate. The extract was washed successively with water and saturated saline and dried over magnesium sulfate. The solvent was then distilled off under reduced pressure, whereby 2-[(cyclopropylthio)(difluoro)methyl]-2-(2,4-difluorophenyl)oxirane (5.0 g, yield: 86%) was obtained as a pale yellow oil.

$^1$H-NMR(CDCl$_3$, δ):
0.66–0.98(4H,m), 1.93–2.25(1H,m), 2.95–2.98(1H,m), 3.48(1H,d,J=5 Hz), 6.71–6.99(2H,m), 7.40–7.65(1H,m).

EXAMPLE 5

Synthesis of 2-[(cyclopropylthio)(difluoro)methyl]-2-(4-fluorophenyl)oxirane [Compound (3-2)]

In a similar manner to Example 4 except for the use of 2-cyclopropylthio-2,2,4'-trifluoroacetophenone instead of 2-cyclopropylthio-2,2,2',4'-tetrafluoroacetophenone, 2-[(cyclopropylthio)(difluoro)methyl]-2-(4-fluorophenyl) oxirane was obtained as a pale yellow oil.

$^1$H-NMR(CDCl$_3$, δ)
0.57–1.03(4H,m), 1.94–2.21(1H,m), 2.81–2.90(1H,m), 3.46(1H,d,J=5 Hz), 6.91–7.15(2H,m), 7.44–7.60(2H,m).

EXAMPLE 6

Synthesis of 2-[(cyclopropylthio)(difluoro)methyl]-2-(4-trifluoromethyl)phenyloxirane (Compound (3-3)]

In a similar manner to Example 4 except for the use of 2-cyclopropylthio-2,2-difluoro- 4'-(trifluoromethyl)acetophenone instead of 2-cyclopropylthio-2,2,2',4'-tetrafluoroacetophenone, 2-[(cyclopropylthic)(difluoro) methyl]-2-(4-trifluoromethylphenyl)oxirane was obtained as a pale yellow oil.

$^1$H-NMR(CDCl$_3$, δ):
0.59–1.04(4H,m), 2.00–2.12(1H,m), 2.80–2.89(1H,m), 3.50(1H,d,J=6 Hz), 7.65(4H,br.s).

EXAMPLE 7

Synthesis of 1-(cyclopropylthio)-2-(2,4-difluorophenyl)-1,1-difluoro-3-(1H-1,2,4-triazol-1-yl)-2-propanol [Compound (1a-1)]

To a solution of 2-[(cyclopropylthio) (difluoro)-methyl]-2-(2,4-difluorophenyl)oxirane (5.0 g, 0.017 mol) in DMSO (70 ml), 1,2,4-triazole (3.48 g, 0.05 mol) and potassium carbonate (6.95 g, 0.05 mol) were added, followed by stirring at 55° C. for 1.5 hours. After the completion of the reaction, water was added to the reaction mixture. The resulting mixture was extracted with ethyl acetate. The extract was washed successively with water and saturated saline and dried over magnesium sulfate. The solvent was then distilled off under reduced pressure. The residue so obtained was crystallized from isopropyl ether—ethyl acetate, whereby 1-(cyclopropylthio)-2-( 2,4-difluorophenyl)-1,1-difluoro-3-(1H-1,2,4-triazol-1-yl)-2-propanol (2.35 g, yield: 32%) was obtained as colorless crystals.

Melting point: 99 to 102° C. IR(KBr) $\upsilon_{max}$cm$^{-1}$: 3111, 1685, 1508, 1148 MS(FAB) : 348(M+H)
$^1$H-NMR(CDCl$_3$, δ):
0.58–1.06(4H,m), 1.89–2.14(1H,m), 4.79(1H,d,J=14 Hz), 5.28(1H,d,J=14 Hz), 5.65(1H,s), 6.60–6.95(2H,m), 7.58–7.85(1H,m), 7.81(1H,s), 8.08(1H,s).

EXAMPLE 8

Synthesis of 1-(cyclopropylthio)-1,1-difluoro-2-(4-fluorophenyl)-3-(1H-1,2,4-triazol-1-yl)-2-propanol [Compound (1a-2)]

In a similar manner to Example 7 except for the use of 2-[(cyclopropylthio)(difluoro)methyl]-2-(4-fluorophenyl) oxirane instead of 2-[(cyclopropylthio)(difluoro)methyl]-2-(2,4-difluorophenyl)-oxirane, 1-(cyclopropylthio)-1,1-difluoro-2-(4-fluorophenyl)-3-(1H-1,2,4-triazol-1-yl)-2-propanol was obtained as colorless crystals.

Melting point: 101 to 102° C. IR(KBr) $\upsilon_{max}$cm$^{-1}$: 3143, 1607, 1511, 1141 MS(FAB): 330(M+H)
$^1$H-NMR(CDCl$_3$, δ):
0.60–0.94(4H,m), 1.88–2.10(1H,m), 4.68(1H,d,J=15 Hz), 4.90(1H,d,J=15 Hz), 5.26(1H,s), 6.92–7.11(2H,m), 7.44–7.60(2H,m), 7.85(1H,s), 7.91(1H,s).

EXAMPLE 9

Synthesis of 1-(cyclopropylthio)-1,1-difluoro-2-(4-trifluoromethylphenyl)-3-(1H-1,2,4-triazol-1-yl)-2-propanol [Compound (1a-3)]

In a similar manner to Example 7 except for the use of 2-[(cyclopropylthio)(difluoro)methyl]-2-(4- trifluoromethylphenyl)oxirane instead of 2-[(cyclopropylthio)(difluoro)methyl]-2-(2,4-difluorophenyl)-oxirane, 1-(cyclopropylthio)-1,1-difluoro-2-(4-trifluoromethylphenyl)-3-(1H-1,2,4-triazol-1-yl)-2-propanol was obtained as colorless crystals.

Melting point: 114 to 115° C. IR(KBr) $\upsilon_{max}$cm$^{-1}$: 3140, 1621, 1514, 1139 MS(FAB): 380(M+H)

$^1$H-NMR(CDCl$_3$, δ):

0.55–1.03(4H,m), 1.85–2.18(1H,m), 4.68(1H,d,J=14 Hz), 4.90(1H,d,J=14 Hz), 5.70(1H,s), 7.46–7.76(4H,m), 7.81 (1H,s), 7.94(1H,s).

EXAMPLE 10

Synthesis of 1-[3-(cyclopropylthio)-2-(2,4-difluorophenyl)-3,3-difluoro-2-methoxypropyl]-1H-1,2,4-triazole [Compound (1a-4)]

To a solution of 60% sodium hydride (75 mg, 1.87 mmol) in N,N-dimethylformamide (50 ml), 1-(cyclopropylthio)-2-(2,4-difluorophenyl)-1,1-difluoro-3-(1H-1,2,4-triazol-1-yl)-2-propanol (0.50 g, 1.44 mmol) was added dropwise under ice cooling, followed by stirring at room temperature for 30 minutes. Methyl iodide (270 mg, 1.87 mmol) was then added dropwise to the reaction mixture under ice cooling and the resulting mixture was stirred at room temperature for 1 hour. Water was added to the reaction mixture, followed by extraction with ether. The ether solution was washed with water and dried over sodium sulfate. The solvent was then distilled off under reduced pressure. The residue was subjected to a silica gel column and from the chloroform eluate fraction, 1-[3-(cyclopropylthio)-2-(2,4-difluorophenyl)-3,3-difluoro-2-methoxypropyl]-1H-1,2,4-triazole (0.31 g, yield: 60%) was obtained as a colorless oil.

MS(FAB): 362(M+H)

$^1$H-NMR(CDCl$_3$, δ):

0.54–0.98(4H,m), 1.85–2.10(1H,m), 3.70(3H,fine t,J=2 Hz), 5.09(2H,t,J=15 Hz), 6.65–6.94(2H,m), 7.46–7.66(1H,m), 7.78(1H,s), 7.98(1H,s)

EXAMPLE 11

Synthesis of 1-[2-(benzyloxy)-3-(cyclopropylthio)-2-(2,4-difluorophenyl)-3,3-difluoropropyl]-1H-1,2,4-triazole [Compound (1a-5)]

In a similar manner to Example 10 except for the use of benzyl chloride instead of methyl iodide, 1-[2-(benzyloxy)-3-(cyclopropylthio)-2-(2,4-difluorophenyl)-3,3-difluoropropyl]-1H-1,2,4-triazole was obtained as a colorless oil.

MS(FAB): 438(M+H)

$^1$H-NMR(CDCl$_3$, δ):

0.56–0.99(4H,m), 1.93–2.18(1H,m), 4.85(1H,d,J=14 Hz), 5.13(1H,d,J=14 Hz), 5.21(1H,br.s), 6.69–6.90(2H,m), 7.38(5H,s), 7.46–7.64(1H,m), 7.77(1H,s), 7.93(1H,s).

EXAMPLE 12

Synthesis of 1-(cyclopropylsulfonyl)-2-(2,4-difluorophenyl)-1,1-difluoro-3-(1H-1,2,4-triazol-1-yl)-2-propanol [Compound (1c-1)]

To a solution of 1-(cyclopropylthio)-2-(2,4-difluorophenyl)-1,1-difluoro-3-(1H-1,2,4-triazol-1-yl)-2-propanol (2.3 g, 6.63 mmol) in dichloromethane (200 ml), 85% m-chloroperbenzoic acid (3.6 g, 14.58 mmol) was added at room temperature, followed by stirring at room temperature for 12 hours. After the completion of the reaction, a saturated aqueous solution of sodium thiosulfate and a saturated aqueous solution of sodium bicarbonate were added and the resulting mixture was stirred. The dichloromethane solution was separated and after washing with water, dried over magnesium sulfate. The solvent was then distilled off under reduced pressure. The residue so obtained was crystallized from isopropyl ether—ethyl acetate, whereby 1-(cyclopropylsulfonyl)-2-(2,4-difluorophenyl)-1,1-difluoro-3-(1H-1,2,4-triazol-1-yl)-2-propanol (1.9 g, yield: 76%) was obtained as colorless crystals.

Melting point: 155 to 156° C. IR(KBr) $\upsilon_{max}$cm$^{-1}$: 3111, 1613, 1504, 1346 MS (FAB) : 380 (M+H)

$^1$H-NMR(CDCl$_3$, δ):

1.12–1.45(4H,m), 2.67–2.73(1H,m), 5.19(1H,d,J=14 Hz), 5.33(1H,d,J=14 Hz), 5.92(1H,s), 6.65–6.93(2H,m), 7.67–7.73(1H,m), 7.79(1H,s), 8.07(1H,s).

EXAMPLE 13

Synthesis of 1-(cyclopropylsulfonyl)-2-(4-fluorophenyl)-1,1-difluoro-3-(1H-1,2,4-triazol-1-yl)-2-propanol [Compound (1c-2)]

In a similar manner to Example 12 except for the use of 1-(cyclopropylthio)-2-(4-fluorophenyl)-1,1-difluoro-3-(1H-1,2,4-triazol-1-yl)-2-propanol instead of 1-(cyclopropylthio)-2-(2,4-difluorophenyl)-1,1-difluoro-3-(1H-1,2,4-triazol-1-yl)-2-propanol, 1-(cyclopropylsulfonyl)-2-(4-fluorophenyl)-1,1-difluoro-3-(1H-1,2,4-triazol-1-yl)-2-propanol was obtained as colorless crystals.

Melting point: 197 to 199° C. IR(KBr) $\upsilon_{max}$cm$^{-1}$: 3088, 1604, 1508, 1333 MS(FAB): 362(M+H)

$^1$H-NMR(CDCl$_3$, δ):

1.10–1.18(4H,m), 2.77–2.81(1H,m), 4.99(1H,d,J=15 Hz), 5.14(1H,d,J=15 Hz), 7.09–7.14(2H,m), 7.54–7.58(2H,m), 7.72(1H,s), 8.21(1H,s).

EXAMPLE 14

Synthesis of 1-(cyclopropylsulfonyl)-1,1-difluoro-2-(4-trifluoromethylphenyl)-3-(1H-1,2,4-triazol-1-yl)-2-propanol [Compound (1c-3)]

In a similar manner to Example 12 except for the use of 1-(cyclopropylthio)-1,1-difluoro-2-(4-trifluoromethylphenyl)-3-(1H-1,2,4-triazol-1-yl)-2-propanol instead of 1-(cyclopropylthio)-2-(2,4-difluorophenyl)-1,1-difluoro-3-(1H-1,2,4-triazol-1-yl)-2-propanol, 1-(cyclopropylsulfonyl)-1,1-difluoro-2-(4-trifluoromethylphenyl)-3-(1H-1,2,4-triazol-1-yl)-2-propanol was obtained as colorless crystals.

Melting point: 194 to 195° C. IR(KBr) $\upsilon_{max}$cm$^{-1}$: 3080, 1620, 1514, 1324 MS(FAB): 412(M+H)

$^1$H-NMR(CDCl$_3$, δ):

1.12–1.21(4H,m), 5.03(1H,d,J=15 Hz), 5.20(1H,d,J=15 Hz), 5.56(1H,s), 7.66(2H,d,J=8 Hz), 7.70(1H,s), 7.75(2H,d,J=8 Hz), 8.26(1H,s).

EXAMPLE 15

Synthesis of 1-[3-(cyclopropylsulfonyl)-2-(2,4-difluorophenyl)-3,3-difluoro-2-methoxypropyl]-1H-1,2,4-triazole [Compound (1c-4)]

In a similar manner to Example 12 except for the use of 1-[3-(cyclopropylthio)-2-(2,4-difluorophenyl)-3,3-difluoro- 2-methoxypropyl]-1H-1,2,4-triazole instead of 1-(cyclopropylthio)-2-(2,4-difluorophenyl)-1,1-difluoro-3-(1H-1,2,4-triazol-1-yl)-2-propanol, 1-[3-(cyclopropylsulfonyl)-2-(2,4-difluorophenyl)-3,3-difluoro-2-methoxypropyl]-1H-1,2,4-triazole was obtained as a colorless oil.
MS(FAB) : 394(M+H)
$^1$H-NMR(CDCl$_3$, δ):
1.11–1.47(4H,m), 2.46–2.62(1H,m), 3.75(3H,s),
5.11(1H,d,J=15 Hz), 5.36(1H,d,J=15 Hz), 6.68–6.98(2H, m),
7.45–7.72(1H,m), 7.79(1H,s), 8.08(1H,s).

EXAMPLE 16

Synthesis of 1-[2-(benzyloxy)-3-(cyclopropylsulfonyl)-2-(2,4-difluorophenyl)-3,3-difluoropropyl]-1H-1,2,4-triazole [Compound (1c-5)]

In a similar manner to Example 12 except for the use of 1-[2-(benzyloxy)-3-(cyclopropylthio)-2-(2,4-difluorophenyl)-3,3-difluoropropyl]-1H-1,2,4-triazole instead of 1-(cyclopropylthio)-2-(2,4-difluorophenyl)-1,1-difluoro-3-(1H-1,2,4-triazol-1-yl)-2-propanol, 1-[2-(benzyloxy)-3-(cyclopropylsulfonyl)-2-(2,4-difluorophenyl)-3,3-difluoropropyl]-1H-1,2,4-triazole was obtained as colorless crystals.
Melting point: 124 to 125° C. IR(KBr) $\upsilon_{max}$cm$^{-1}$: 1616, 1499, 1347 (FAB) : 470(M+H)
$^1$H-NMR(CDCl$_3$, δ):
1.10–1.15(2H,m), 1.33–1.37(2H,m), 2.50–2.54(1H,m),
5.02(1H,d,J=10 Hz), 5.11(1H,d,J=10 Hz), 5.31(1H,d,J=15 Hz),
5.45(1H,d,J=15 Hz), 6.80–6.87(2H,m), 7.31–7.46(5H,m),
7.58–7.64(1H,m), 7.79(1H,s), 8.02(1H,s).

EXAMPLE 17

Optical resolution of 1-(cyclopropylsulfonyl)-2-(2,4-difluorophenyl)-1,1-difluoro-3-(1H-1,2,4-triazol-1-yl)-2-propanol (±)-1-(Cyclopropylsulfonyl)-2-( 2,4-difluorophenyl)-1,1-difluoro-3-(1H-1,2,4-triazol-1-yl)-2-propanol (30 mg) was subjected to CHIRALCEL OD (trade name; product of Daicel Chemical Industries, Ltd.), that is, a column for the separation of an optically active substance. From the eluate fraction of a 4:1 hexane—isopropyl alcohol mixture, 14 mg (optical purity: 100% e.e.) of the (+) form as colorless crystals and 13 mg (optical purity: 100% e.e.) of the (−) form as colorless crystals were obtained in the order of elution.
(1) (+)-1-(Cyclopropylsulfonyl)-2-(2,4-difluorophenyl)-1,1-difluoro-3-(1H-1,2,4-triazol-1-yl)-2-propanol $[α]_D^{21.7}$+22.5° (C=0.1, acetone)
Melting point: 130 to 132° C. IR(KBr) $\upsilon_{max}$cm$^{-1}$: 3111, 1613, 1504, 1346 MS(FAB): 380(M+H)
$^1$H-NMR(CDCl$_3$, δ):
1.12–1.45(4H,m), 2.67–2.73(1H,m), 5.19(1H,d,J=14 Hz),
5.33(1H,d,J=14 Hz), 5.92(1H,s), 6.65–6.93(2H,m),
7.67–7.73(1H,m), 7.79(1H,s), 8.07(1H,s).
(2) (−)-1-(Cyclopropylsulfonyl)-2-(2,4-difluorophenyl)-1,1-difluoro-3-(1H,1,2,4-triazol-1-yl)-2-propanol $[α]_D^{21.7}$ −24.5° (C=0.1, acetone)
Melting point: 130 to 132° C. IR(KBr) $\upsilon_{max}$cm$^{-1}$: 3111, 1613, 1504, 1346 MS(FAB): 380(M+H)
$^1$H-NMR(CDCl$_3$, δ):
1.12–1.45(4H,m), 2.67–2.73(1H,m), 5.19(1H,d,J=14 Hz),
5.33(1H,d,J=14 Hz), 5.92(1H,s), 6.65–6.93(2H,m),
7.67–7.73(1H,m), 7.79(1H,s), 8.07(1H,s).

EXAMPLE 18

Optical resolution of 1-(cyclopropylsulfonyl)-2-(4-fluorophenyl)-1,1-difluoro-3-(1H-1,2,4-triazol-1-yl)-2-propanol (±)-1-(Cyclopropylsulfonyl)-2-(4-difluorophenyl)-1,1-difluoro-3-(1H-1,2,4-triazol-1-yl)-2-propanol (30 mg) was subjected to CHIRALCEL OD (trade name; product of Daicel Chemical Industries, Ltd.), that is, a column for the separation of an optically active substance. From the eluate fraction of a 2:1 hexane—isopropyl alcohol mixture, 10 mg (optical purity: 100% e.e.) of the (+) form as colorless crystals and 10 mg (optical purity: 100% e.e.) of the (−) form as colorless crystals were obtained in the order of elution.
(1) (+)-1-(Cyclopropylsulfonyl)-2-(4-fluorophenyl)-1,1-difluoro-3-(1H-1,2,4-triazol-1-yl)-2-propanol $[α]_D^{21.7}$ +22.5° (C=0.1, acetone)
Melting point: 144 to 145° C. IR(KBr) $\upsilon_{max}$cm$^{-1}$: 3122, 1605, 1514, 1332 MS(FAB): 362(M+H)
$^1$H-NMR(CDCl$_3$, δ):
1.10–1.18(4H,m), 2.77–2.81(1H,m), 4.99(1H,d,J=15 Hz),
5.14(1H,d,J=15 Hz), 7.09–7.14(2H,m), 7.54–7.58(2H,m),
7.72(1H,s), 8.21(1H,s).
(2) (−)-1-(Cyclopropylsulfonyl)-2-(4-fluorophenyl)-1,1-difluoro-3-(1H-1,2,4-triazol-1-yl)-2-propanol $[α]_D^{21.7}$ −23.5° (C=0.1, acetone)
Melting point: 145 to 146° C. IR(KBr) $\upsilon_{max}$cm$^{-1}$: 3122, 1605, 1514, 1332 MS(FAB) : 362(M+H)
$^1$H-NMR(CDCl$_3$, δ):
1.10–1.18(4H,m), 2.77–2.81(1H,m), 4.99(1H,d,J=15 Hz),
5.14(1H,d,J=15 Hz), 7.09–7.14(2H,m), 7.54–7.58(2H,m),
7.72 (1H,s) , 8.21 (1H,s).
Test 1: Action against *Candida albicans* (in vitro)

To each well of a 96-well microtiter plate, 75 μl of a dilute medicament solution adjusted with a 10% fetalbovine-serum added MEM medium (containing glutamine and a carbonate) were poured, followed by the addition of 75 μl of 4×10$^4$ cells/ml of *C. albicans* ATCC 44859 suspended in the same medium. The resulting mixture was incubated at 37° C. for 24 hours in a CO$_2$ gas incubator. After incubation, a morphological change of *C. albicans* was observed under an inverted microscope. The minimum medicament concentration permitting the apparent suppression of mycerial type growth compared with that of a medicament-free control was designated as a terminal point (ng/ml). Incidentally, as a medicament for comparison, Fluconazole and known compound A [(−)-compound (1c-1) in Japanese Patent Application Laid-Open No. HEI 9–2275313] were employed. The results are shown in Table 1.
Test 2: Action against *Aspergillus fumigatus* (in vitro)

To each well of a 96-well microtiter plate, 100 μl of a dilute medicament solution adjusted with 0.165M MOPS-containing RPMI 1640 medium (containing glutamine and phenol red, carbonate free; pH 7) were poured, followed by the addition of 100 μl of 6.0×10$^4$ conidia/ml of an *A. fumigatus* IFM 40808 spore suspension in the above medium containing 20% almar Blue. They were incubated at 35° C. for 48 hours. Judgment was made visually and the minimum medicament concentration which did not cause a change of color of the medium into red (at which the color of the medium was still maintained blue) was designated as an MIC value (μg/ml). Incidentally, as a medicament for comparison, Fluconazole and known compound A ((−)-compound (1c-1) in Japanese Patent Application Laid-Open No. HEI 9-227531) were employed. The results are shown in Table 1.

TABLE 1

|  | Terminal point (ng/ml) | MIC (μg/ml) |
| --- | --- | --- |
| Test compound | C. albicans | A. fumigatus |
| Example 7 | 7.8 | 2 |
| Example 8 | 15.6 | 8 |
| Example 10 | 31.3 | 32 |
| Example 12 | 31.3 | 8 |
| Example 17(2) | 15.6 | 2 |
| Fluconazole | 250 | >128 |
| Known compound A | 62.5 | 16 |

Test 3: Action against *Candida albicans* (in vivo)

After 4-week-old, male, ICR (CRJ: CD-1) mice were fasted for 6 hours, *C. albicans* IFM 40009 was inoculated to the tail vein of each of the mice to give an amount of $3.0 \times 10^6$ cells/mouse, whereby infection was caused. A control group consisted of 11 mice, while a medicament-administered group consisted of 5 mice. The medicament dissolved in 20% polyethylene glycol was orally administered 1 hour after the inoculation of the fungus and from 24 hours after the inoculation, it was administered once a day for 4 straight days, each in an amount of 1.25 mg/kg. The survival condition on Day 14 after the infection was compared. In addition, the survival days of the control group and the medicament-administered group were detected by the Kaplan-Meier method (Cox mantel test). Incidentally, Fluconazole was employed as a medicament for comparison. The results are shown in Table 2.

TABLE 2

| Test compound | Average Survival days | Surviving mice on Day 14 number of surviving mice / total number in group |
| --- | --- | --- |
| Example 12 | 14.00*** | 4/5 |
| Example 15 | 13.4*** | 4/5 |
| Fluconazole | 11.0*** | 1/5 |
| Control | 4.5 | 9/11 |

(relative to control: ***p<0.001)

EXAMPLE 19

Tablets

| Compound of Example 17(2) | 50 mg |
| --- | --- |
| Crystalline cellulose | 50 mg |
| Lactose | 50 mg |
| Hydroxypropyl cellulose | 18 mg |
| Magnesium stearate | 2 mg |
| Total | 170 mg |

In a conventional manner, tablets having the above-described composition were prepared. The tablets can be formed as sugar coated tablets or film coated tablets as needed.

EXAMPLE 20

Capsules

| Compound of Example 17(2) | 50 mg |
| --- | --- |
| Light silicic anhydride | 25 mg |
| Lactose | 100 mg |
| Starch | 50 mg |
| Talc | 25 mg |
| Total | 250 mg |

The above ingredients were filled in No. 1 capsules, whereby capsules were obtained.

EXAMPLE 21

Granules

| Compound of Example 17(2) | 50 mg |
| --- | --- |
| Lactose | 600 mg |
| Corn starch | 200 mg |
| Carboxymethyl cellulose sodium | 20 mg |
| Hydroxypropyl cellulose | 130 mg |
| Total | 1000 mg |

In a conventional manner, granules having the above-described composition were prepared.

EXAMPLE 22

Powders

| Compound of Example 17(2) | 50 mg |
| --- | --- |
| Light silicic anhydride | 20 mg |
| Precipitated calcium carbonate | 10 mg |
| Lactose | 250 mg |
| Starch | 70 mg |
| Total | 400 mg |

In a conventional manner, powders having the above-described composition were prepared.

EXAMPLE 23

Injection

| Compound of Example 17(2) | 5 mg |
| --- | --- |
| Hydrogenated castor oil | 85 mg |
| Propylene glycol | 60 mg |
| Glucose | 50 mg |
| Distilled water for injection | q. s. |
| Total | 1 ml |

In a conventional manner, an injection having the above-described composition was prepared.

EXAMPLE 24

Intravenous Drip Infusion

| | |
|---|---|
| Compound of Example 17(2) | 50 mg |
| Hydrogenated castor oil | 5 g |
| Propylene glycol | 10 mg |
| Glucose | 14.5 mg |
| Distilled water for injection | q. s. |
| Total | 100 ml |

An intravenous drip infusion having the above-described composition was prepared in a conventional manner.

What is claimed is:

1. A 2,2-difluoro-2-cyclopropylthioacetophenone derivative represented by the following formula (2):

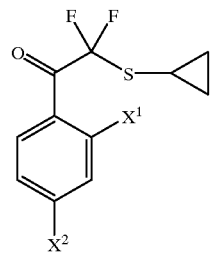

(2)

wherein $X^1$ and $X^2$ are the same or different and each independently represents a hydrogen atom, a halogen atom or a halogenoalkyl group having 1 to 6 carbon atoms.

* * * * *

UNITED STATES PATENT AND TRADEMARK OFFICE
CERTIFICATE OF CORRECTION

PATENT NO. : 6,172,266

DATED : Jan. 9, 2001

INVENTOR(S): Sunao TAKEDA, et al.

It is certified that an error appears in the above-identified patent and that said Letters Patent is hereby corrected as shown below:

On the Title page, Item (54), and at the top of Column 1, the title should be:

-- (54) TRIAZOLE DERIVATIVE OR SALT THEREOF, PREPARATION PROCESS THEREOF AND PHARMACEUTICAL CONTAINING SAID COMPOUND AS AN EFFECTIVE INGREDIENT --

Signed and Sealed this

Eighth Day of May, 2001

Attest:

NICHOLAS P. GODICI

Attesting Officer

Acting Director of the United States Patent and Trademark Office